US011627816B2

(12) United States Patent
Bullard et al.

(10) Patent No.: US 11,627,816 B2
(45) Date of Patent: Apr. 18, 2023

(54) AUTOMATICALLY ADJUSTING COMFORT SYSTEM

(71) Applicant: Textron Innovations, Inc., Providence, RI (US)

(72) Inventors: Michael Allen Bullard, Wichita, KS (US); Samantha Moore Wilt, Wichita, KS (US); Craig Daniel Cillessen, Wichita, KS (US)

(73) Assignee: Textron Innovations, Inc., Providence, RI (US)

( * ) Notice: Subject to any disclaimer, the term of this patent is extended or adjusted under 35 U.S.C. 154(b) by 766 days.

(21) Appl. No.: 15/872,115

(22) Filed: Jan. 16, 2018

(65) Prior Publication Data

US 2018/0199729 A1 Jul. 19, 2018

Related U.S. Application Data

(60) Provisional application No. 62/446,614, filed on Jan. 16, 2017.

(51) Int. Cl.
*B64D 11/00* (2006.01)
*A47C 31/12* (2006.01)
(Continued)

(52) U.S. Cl.
CPC ............ *A47C 31/126* (2013.01); *A47C 1/031* (2013.01); *A47C 7/029* (2018.08); *A47C 7/14* (2013.01);
(Continued)

(58) Field of Classification Search
CPC .......... B64D 11/0639; B64D 11/06395; B64D 11/064; B64D 11/0641; B64D 11/0642;
(Continued)

(56) References Cited

U.S. PATENT DOCUMENTS 3,019,784 A * 2/1962 Eiden .................... A47C 21/048
601/58
5,170,364 A * 12/1992 Gross ..................... A47C 27/10
297/284.6
(Continued)

FOREIGN PATENT DOCUMENTS

WO 2005074754 A1 8/2005

OTHER PUBLICATIONS

Lorenzo Sadun "Net change theorem" Dec. 10, 2012 https://www.youtube.com/watch?v=9vWSdW9-ISU&feature=emb_logo (Year: 2012).*

*Primary Examiner* — Philip R Wiest
*Assistant Examiner* — Tyler A Raubenstraw
(74) *Attorney, Agent, or Firm* — Avek IP, LLC

(57) ABSTRACT

An automatically adjusting comfort method includes measuring pressure applied by a user via a pressure-sensor array, determining a pressure profile based on measurements from the pressure-sensor array, comparing the pressure profile to a first limit, determining a cumulative pressure profile over a predetermined duration, comparing the cumulative pressure profile to a second limit, and adjusting one or more of a plurality of adjusting mechanisms configured to alter the pressure profile for increased comfort of the user when the pressure profile exceeds the first limit or the second limit. An automatically adjusting comfort system includes a pressure-sensor array communicatively coupled to a controller for determining a cumulative pressure profile over time, and a plurality of adjusting mechanisms configured to alter the pressure profile to increase a user's comfort, wherein the controller automatically adjusts one or more of the plurality of adjusting mechanisms based on the cumulative pressure profile.

20 Claims, 5 Drawing Sheets

(51) Int. Cl.
*A47C 1/031* (2006.01)
*A47C 7/46* (2006.01)
*A47C 7/14* (2006.01)
*A47C 7/74* (2006.01)
*B64D 11/06* (2006.01)
*A61F 7/00* (2006.01)
*A61G 5/12* (2006.01)
*A61H 9/00* (2006.01)
*A47C 7/02* (2006.01)
*A61G 7/057* (2006.01)
*A61G 5/10* (2006.01)
*A61H 15/00* (2006.01)

(52) U.S. Cl.
CPC .............. *A47C 7/142* (2018.08); *A47C 7/144* (2018.08); *A47C 7/46* (2013.01); *A47C 7/74* (2013.01); *A61F 7/00* (2013.01); *A61G 5/10* (2013.01); *A61G 5/122* (2016.11); *A61G 7/057* (2013.01); *A61G 7/05707* (2013.01); *A61G 7/05769* (2013.01); *A61H 9/0078* (2013.01); *A61H 15/0078* (2013.01); *B64D 11/0626* (2014.12); *B64D 11/0639* (2014.12); *B64D 11/0689* (2013.01); *A61F 2007/0093* (2013.01); *A61G 5/124* (2016.11); *A61G 2203/34* (2013.01); *A61H 2201/0103* (2013.01); *A61H 2201/0134* (2013.01); *A61H 2201/0142* (2013.01); *A61H 2201/0149* (2013.01); *A61H 2201/0192* (2013.01); *A61H 2201/0242* (2013.01); *A61H 2201/10* (2013.01); *A61H 2201/1623* (2013.01); *A61H 2201/1633* (2013.01); *A61H 2201/5071* (2013.01); *A61H 2203/0431* (2013.01); *A61H 2203/0443* (2013.01); *A61H 2205/081* (2013.01); *A61H 2230/625* (2013.01)

(58) Field of Classification Search
CPC ............ B64D 11/0643; B64D 11/0644; B64D 11/0626; B64D 11/0689; B64D 13/00; A47C 31/12; A47C 31/123; A47C 31/126; A47C 31/14; A47C 7/142; A47C 1/031; A47C 7/14; A47C 7/46; A47C 7/74; A61H 2201/5071; A61H 2201/0149; A61H 2230/625; A61H 9/0078; A61H 2201/10; G01L 1/02; A61G 5/122; A61G 2203/34; A61F 7/00; A61F 2007/0093; A47F 7/00

See application file for complete search history.

(56) References Cited

U.S. PATENT DOCUMENTS

| | | | |
|---|---|---|---|
| 5,587,933 A * | 12/1996 | Gross | A61H 7/00 364/558 |
| 5,930,152 A | 7/1999 | Dumont et al. | |
| 6,094,762 A | 8/2000 | Viard et al. | |
| 7,152,920 B2 * | 12/2006 | Sugiyama | A47C 7/14 297/284.6 |
| 8,477,039 B2 * | 7/2013 | Gleckler | A61B 5/4561 340/573.7 |
| 8,585,146 B1 * | 11/2013 | Giasson | B64D 11/0643 297/344.21 |
| 9,009,898 B2 | 4/2015 | Morimura et al. | |
| 2006/0094993 A1 * | 5/2006 | Hazard | A61H 7/00 601/98 |
| 2008/0015719 A1 * | 1/2008 | Ziolek | G06F 30/15 700/97 |
| 2009/0036809 A1 * | 2/2009 | Nishio | A61H 7/00 601/134 |
| 2009/0099490 A1 * | 4/2009 | Durt | A61H 15/00 601/115 |
| 2010/0198121 A1 * | 1/2010 | Tago | A61H 9/00 601/150 |
| 2010/0276973 A1 * | 11/2010 | Zenk | B60N 2/0244 297/284.3 |
| 2011/0006568 A1 * | 1/2011 | Hsu | A47C 7/46 297/217.3 |
| 2011/0115635 A1 * | 5/2011 | Petrovski | B64D 11/0649 297/344.21 |
| 2012/0212018 A1 * | 8/2012 | Ishikawa | A61H 23/006 297/217.1 |
| 2014/0343467 A1 * | 11/2014 | Fukuyama | A61H 9/0078 601/98 |
| 2015/0170494 A1 * | 6/2015 | Hsu | A61B 5/1117 340/539.17 |
| 2015/0297437 A1 * | 10/2015 | Neuenhahn | A61H 1/00 |
| 2015/0366350 A1 * | 12/2015 | Di Censo | A61B 5/1128 700/275 |
| 2016/0015184 A1 | 1/2016 | Nunn et al. | |
| 2016/0317378 A1 * | 1/2016 | Fujishiro | A61H 9/0078 |
| 2016/0183687 A1 * | 6/2016 | Hoyt | A47C 7/56 297/217.2 |
| 2016/0256100 A1 * | 9/2016 | Jacofsky | G16H 40/63 |
| 2017/0151895 A1 * | 6/2017 | Von Ballmoos | B60N 2/0284 |
| 2018/0235377 A1 * | 8/2018 | Choi | G05B 15/02 |

* cited by examiner

AUTOMATICALLY ADJUSTING COMFORT SYSTEM

CROSS-REFERENCE TO RELATED APPLICATIONS

This application claims the benefit of U.S. Provisional Patent Application Ser. No. 62/446,614 entitled Automatically Adjusting Comfort System and filed Jan. 16, 2017, the disclosure of which is herein incorporated by reference in its entirety.

BACKGROUND

1. Field

Embodiments of this disclosure relate generally to systems and methods for enabling sitting or lying comfortably for extended periods of time. Specifically, embodiments relate to the implementation of these systems and methods into seats or beds, e.g., in an aircraft.

2. Description of the Related Art

Seats and beds may be adjusted in a variety of ways to increase a user's comfort. Conventionally, most adjustable seats and beds require manual adjustment of individual components. Some adjustable aircraft seats receive height information from the user and automatically adjust the headrest and leg rest positions accordingly. Other systems may use pressure sensors to evaluate the user's posture in a seat, and a computer provides a recommendation for a different position. The user may then select a different position and the seat will adjust accordingly.

U.S. Pat. No. 5,930,152 to Dumont et al. discloses a device for determining configuration of a seat or the like for positioning a user. The device may determine optimal positioning using pressure mappings and calculated center of gravity and may include an auto-correct mode for managing the position of the chair and providing correction.

International Patent Publication WO-2005/074754 to Burkitt discloses a posture sensing seat to identify unsatisfactory posture and generate an alert. Posture may be estimated by an occupant's center of gravity, and a motorized mechanism may be used to adjust posture automatically.

U.S. Pat. No. 8,477,039 to Glecker et al. discloses a system for producing information about the posture of a user by using an array of sensors associated with a seat.

U.S. Pat. No. 6,094,762 to Viard et al. discloses a system and method for a patient support device having an inflatable chamber, a pressure measurement device, and a controller to regulate chamber pressure.

U.S. Pat. No. 9,009,898 discloses a pressure sensor system for use with a multi-cell air mattress.

U. S. Patent Publication 2016/0015184 to Nunn et al. discloses a system and method for automatically sensing and adjusting pressure of an air mattress and a temperature controller for increasing or decreasing bed temperature.

SUMMARY

In an embodiment, an automatically adjusting comfort method is provided. The method includes measuring pressure applied by a user to a first surface via a pressure-sensor array, determining a pressure profile along the first surface based on measurements from the pressure-sensor array, comparing the pressure profile to a first limit, determining a cumulative pressure profile based on the pressure profile over a predetermined duration, comparing the cumulative pressure profile to a second limit, and adjusting one or more of a plurality of adjusting mechanisms configured to alter the pressure profile for increased comfort of the user when the pressure profile exceeds the first limit or the second limit.

In another embodiment, an automatically adjusting comfort system is provided. The system includes a pressure-sensor array communicatively coupled to a controller for determining a cumulative pressure profile over time, and a plurality of adjusting mechanisms configured to alter the pressure profile to increase a user's comfort, wherein the controller automatically adjusts one or more of the plurality of adjusting mechanisms based on the cumulative pressure profile.

In yet another embodiment, a method of automatically maintaining comfort for extended duration is provided. The method includes measuring pressure applied to a surface of a seat via an array of pressure sensors to determine an array of pressure values in real-time via a controller, weighting the pressure values based on locations of corresponding pressure sensors of the array to determine weighted-pressure values, determining one or more regions of differential pressure based on the weighted-pressure values and a proximity of the corresponding pressure sensors, and adjusting a configuration of the seat for reducing a magnitude of the differential pressure at the one or more regions.

BRIEF DESCRIPTION OF THE DRAWINGS

Illustrative embodiments of the present disclosure are described in detail below with reference to the attached drawing figures, which are incorporated by reference herein and wherein.

DETAILED DESCRIPTION

An automatically adjusting comfort system is intended to solve health and comfort issues related to long duration flights and for patients confined to wheelchairs or beds. Conventional adjustable seats and beds require user input. Embodiments of the present disclosure improve ergonomics and long duration comfort by providing a system and method to automatically determine a user's posture, position, and associated pressure points, and to automatically adjust the user's posture and position to relieve pressure points.

Figure 1:
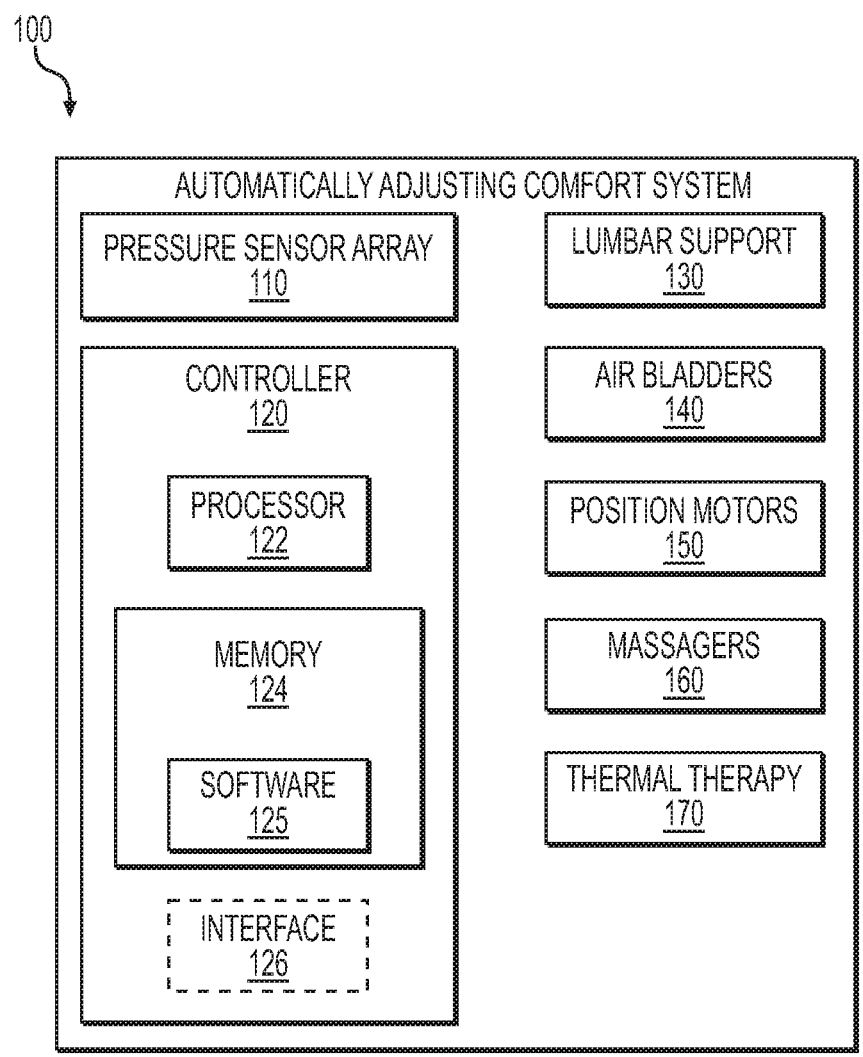
FIG. 1 is a block diagram representing an automatically adjusting comfort system, in an embodiment.

FIG. 1 is a block diagram of an automatically adjusting comfort system 100. System 100 may be a seat, bed, mattress, couch, floor mat, or other device configured to automatically adjust a user's comfort. Adjustments are made based on a pressure profile, which includes some compilation of pressure points, monitored over time. The pressure profile may be compiled from a pressure-sensor array 110 integrated into the user device for providing dynamic real-time pressure information. The user's comfort is increased by adjusting position and/or other means (e.g., massage and temperature control). Adjustments made by system 100 may include lumbar support, firmness, tilt, shape and position, as well as massage and heating/cooling, for example. The automatically adjusting configurations of system 100 encourage dynamic and ergonomically-friendly posture while eliminating the need for the user to manually adjust position.

Sensors of pressure-sensor array 110 may include one or more of pressure transducers, strain gauges, piezoelectric sensors, and optical fibers integrated into system 100 to provide pressure point data from a plurality of locations. A controller 120 receives data from pressure-sensor array 110 and determines a profile of pressure points. The pressure-point profile may be used by the controller to determine adjustments to system 100, as described below in connection with method 400, FIG. 4. System 100 includes components for adjusting position and increasing comfort of the user, such as a lumbar support 130, air bladders 140, position motors 150, massagers 160, and a thermal therapy unit 170.

Controller 120 is for example a computer, microcontroller, microprocessor, or programmable logic controller (PLC) having a memory 124, including a non-transitory medium for storing software 125, and a processor 122 for executing instructions of software 125. An example of software instructions includes a control algorithm 500, described below in connection with FIG. 5. Controller 120 may further include an optional interface 126 for a user to transmit instructions and receive information. Interface 126 may enable the user to input instructions for adjusting system 100 thereby overriding or complementing any automatic adjustments. For example, automatic adjustments may be customized to accommodate personal preferences of individual users. Communication between controller 120 and pressure-sensor array 110 or between controller 120 and other components of system 100, which are described below, may be by one of a wired and/or wireless communication media.

Lumbar support 130 provides an adjustable portion positioned adjacent the user's lower back to automatically adjust support of the user's spinal curvature, based on the pressure point profile. Air bladders 140 may be automatically inflated using a pump and deflated via a release valve to increase and decrease the firmness of system 100, respectively. Position motors 150 may be used to automatically adjust the tilt and position of system 100, such as the tilt and position of a seat back and a seat bottom, for example. Massagers 160 may include motorized rotary parts for massaging muscles of the user, which may be located internally within system 100 or massagers 160 may protrude externally from system 100. Thermal therapy unit 170 includes pads (see e.g., item 275, FIGS. 2 and 3) located inside or adjacent system 100 that are fluidly coupled to a reservoir, and a pump to circulate a fluid, such as water, between the reservoir and at least one of the bladders. A heater and a chiller are coupled to the reservoir for controlling fluid temperature, thereby heating or cooling portions of system 100 under control of controller 120. Thermal therapy unit 170 may optionally include valves for directing flow from the reservoir to a particular bladder or group of bladders based on the pressure point profile.

Figure 2:
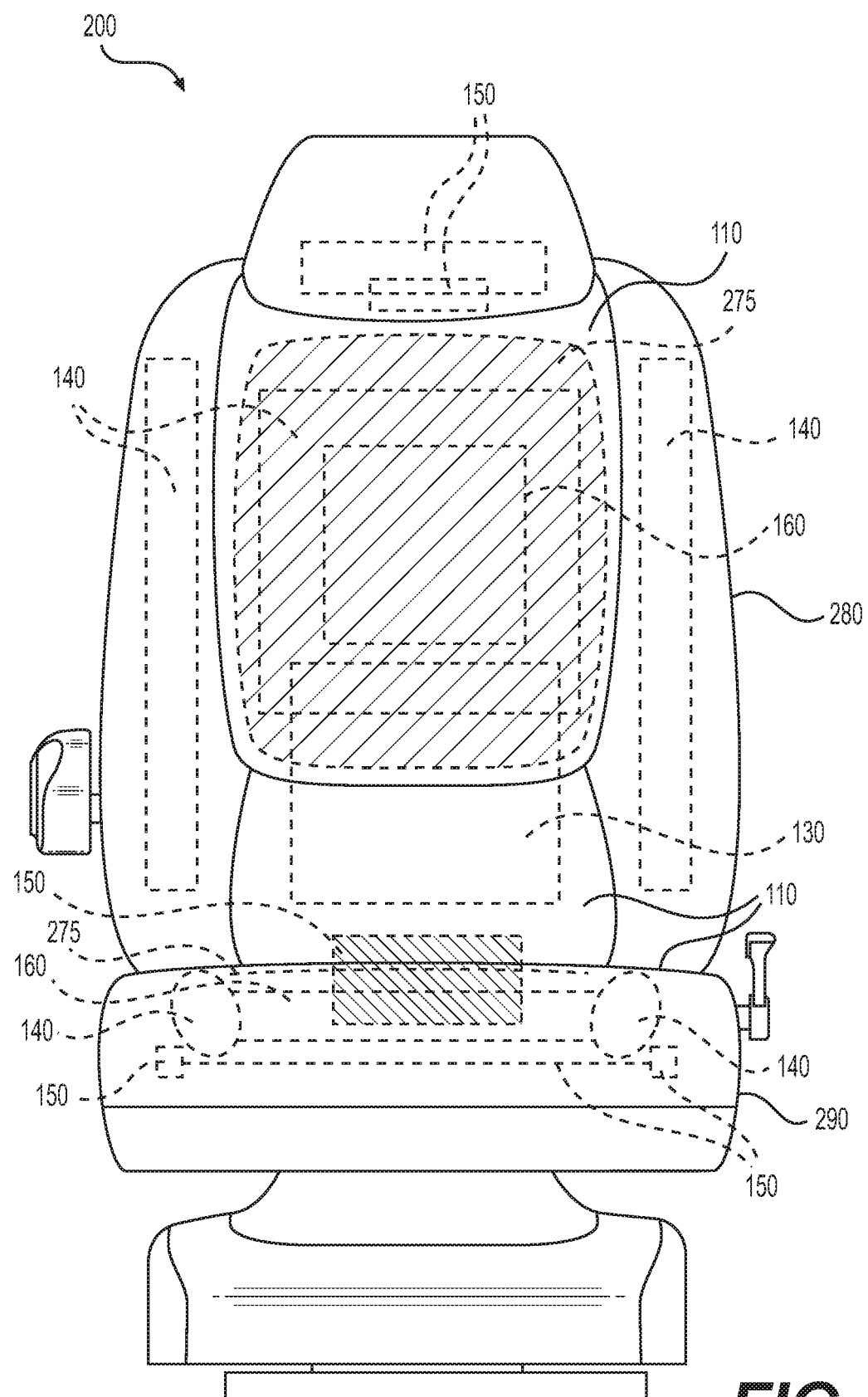
FIG. 2 is a front view of an automatically adjusting comfort system, in an embodiment.
Figure 3:
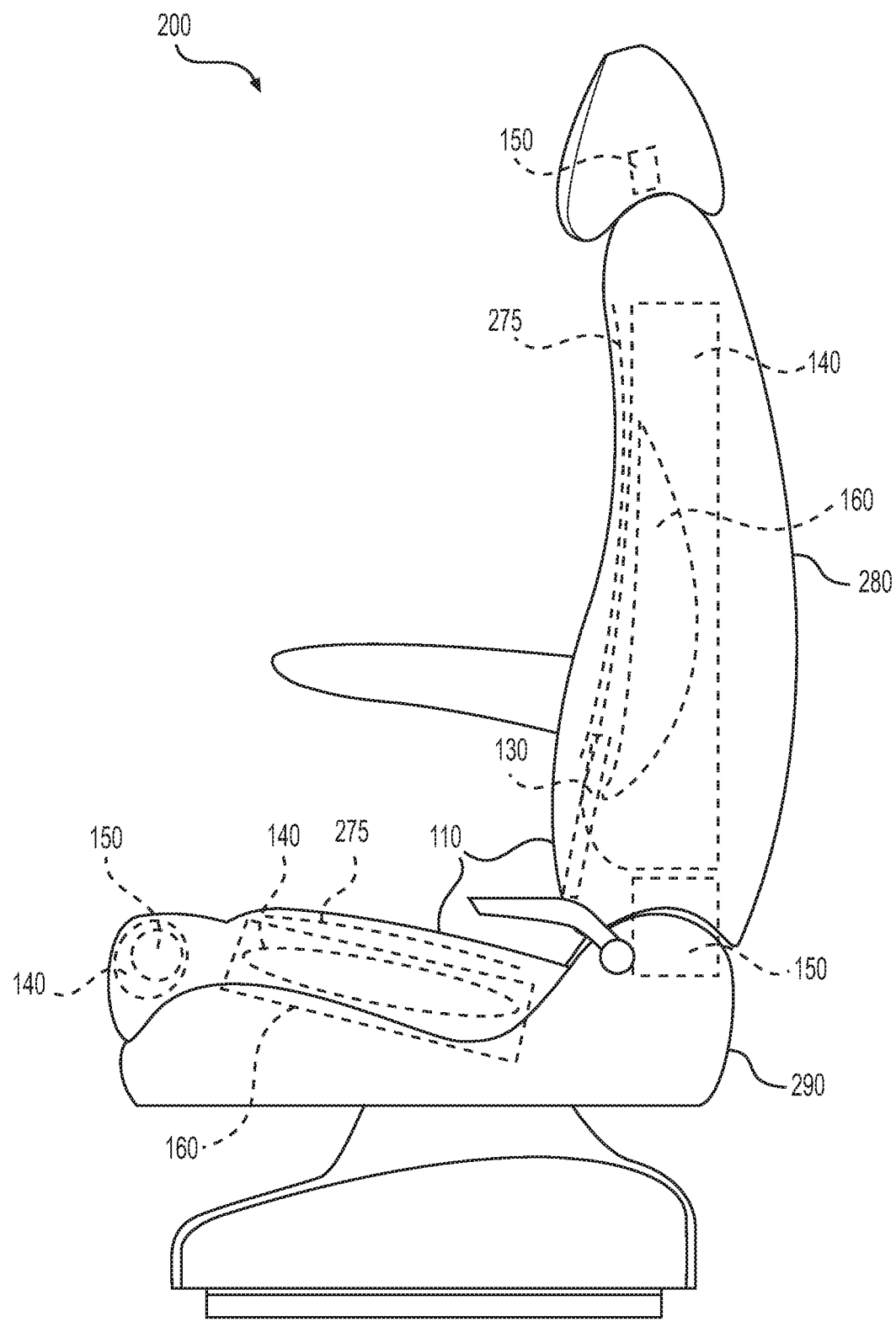
FIG. 3 is a side view of the automatically adjusting comfort system of FIG. 2.

FIG. 2 is a front view of an exemplary automatically adjusting comfort system 200. System 200 is an example of system 100, FIG. 1 configured as a seat having a seat back 280 and a seat bottom 290. In certain embodiments, system 200 is configured as an aircraft pilot or copilot seat. FIG. 3 is a side view of automatically adjusting comfort system 200 of FIG. 2. FIGS. 2 and 3 are best viewed together with the following description.

System 200 may include some or all of the components of system 100 of FIG. 1 for adjusting position and increasing comfort of the user, including an integrated dynamic pressure-sensor array such as pressure-sensor array 110, controller 120 (not shown), lumbar support 130, air bladders 140, position motors 150, massagers 160, and a thermal therapy pad 275 of thermal therapy unit 170 (other parts of thermal therapy unit 170 are not shown). Components located beneath the seat surface are indicated with dashed lines to represent that these components are normally not visible following final seat construction. Pressure-sensor array 110 is indicated with solid lines, as it is preferably located on the surface of seat (e.g., integrated into the outer fabric of the seat). Alternatively, pressure-sensor array 110 may be located just beneath the outer fabric of the seat. The positions of components depicted in FIGS. 2 and 3 are exemplary only and these may be altered without departing from the scope hereof. Many of the components overlap as shown with overlapping dashed lines in FIG. 2, which may be best viewed from FIG. 3.

FIG. 3 provides a side view of automatically adjusting comfort system 200 of FIG. 2 showing overlapping components. For example, in seat back 280, pressure-sensor array 110 may be on the surface, a thin thermal pad 275 may be just behind the surface, and lumbar support 130, air bladders 140, and massagers 160 may be behind thermal pad 275. Massagers 160 may be embedded within foam of seat back 280, for example. Position motors may be located within the skeleton of the seat frame behind lumbar support and beneath air bladders 140. Similarly, in seat bottom 290, pressure-sensor array 110 may be on the surface, a thin thermal pad 275 may be just beneath the surface, and air bladder 140 and massagers 160 may be beneath thermal pad 275, with massagers 160 embedded within foam of seat bottom 290. Other arrangements of overlapping components may be employed without departing from the scope hereof.

Figure 4:
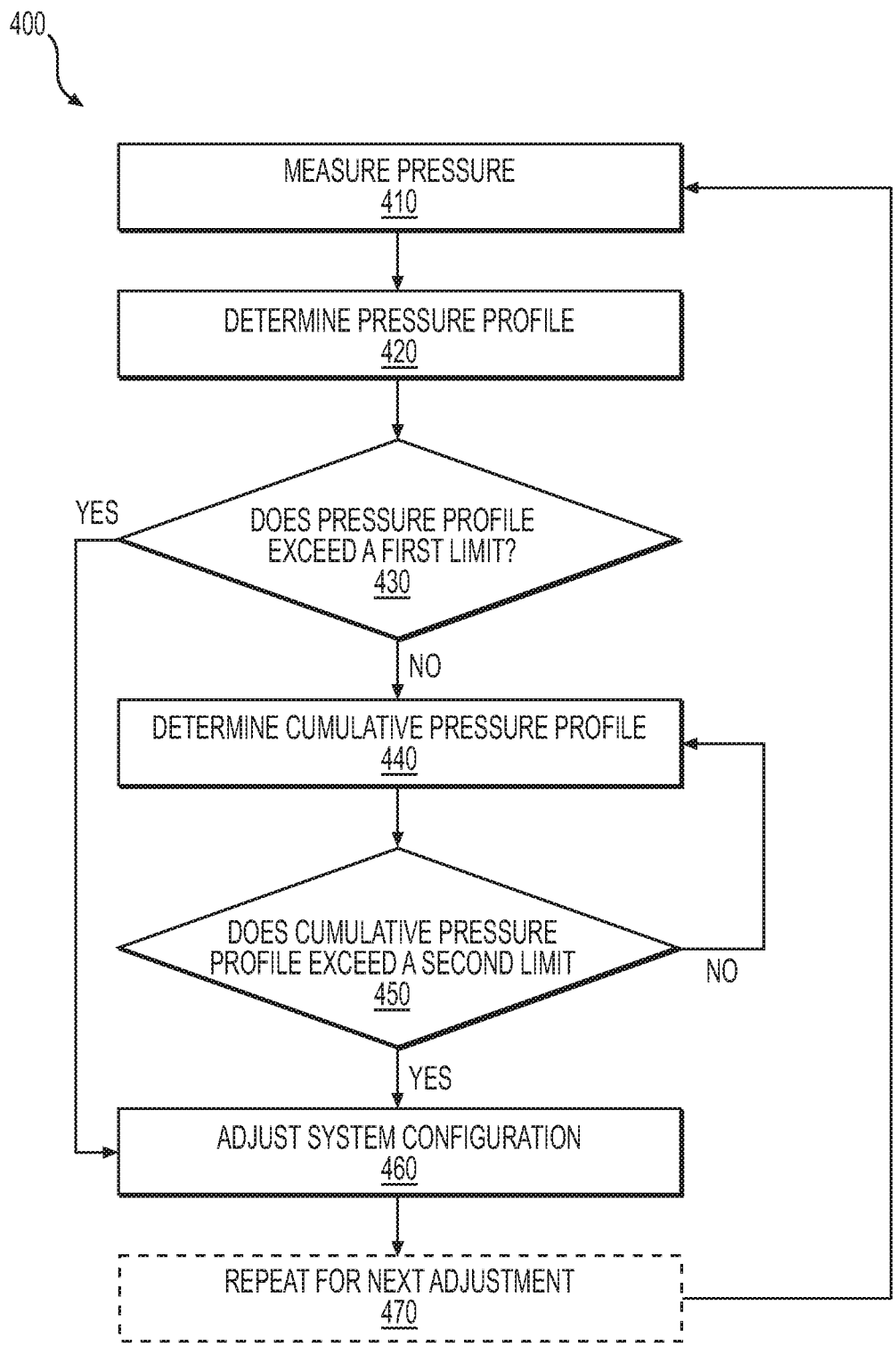
FIG. 4 is a flow diagram of a method for automatically adjusting a comfort system, in an embodiment.

FIG. 4 is a flow diagram of an exemplary method for automatically adjusting a comfort system, such as system 100, FIG. 1.

In a step 410, pressure is measured at a plurality of locations. In an example of step 410, pressure is measured via pressure-sensor array 110, FIG. 1.

In a step 420, a pressure profile is determined. In an example of step 420, instructions of software 125 include an algorithm to determine a pressure profile that includes data from each of the sensors of pressure-sensor array 110 and information about the location of each of the sensors (e.g., a lookup table or map). An exemplary algorithm 500 for determining the pressure profile is described below in connection with FIG. 5 (see e.g., operation 520). The pressure profile provides a compilation of pressure data for determining seating or lying configurations, such as posture and regions of high and low pressure. The pressure profile may take into account both the raw pressure values from each of the pressure sensors and the location of the individual pressure sensors, since pressure distribution will vary based on location. In other words, the pressure values may be weighted (see e.g., operation 510, FIG. 5) based on location within seat 200 or other considerations such as an angle or position of the user device (e.g., an upright versus reclined seating position). The pressure profile may be analyzed as a statistical distribution having statistical properties. For example, a high-pressure region may be identified based on a certain deviation (e.g., two standard-deviations) from an average or a median pressure value. In an embodiment, the pressure profile includes a pressure map of pressure values corresponding to locations of pressure-sensor array 110. The pressure map may be optionally displayed via interface 126, for example.

Step 430 is a decision. If in step 430 the pressure profile from step 420 exceeds a first limit, method 400 proceeds to step 460. Otherwise, method 400 proceeds to step 440. An example of the first limit is a high-pressure value from a single sensor of pressure-sensor array 110. Another example of the first limit is a grouping of high-pressure values from nearby sensors of pressure-sensor array 110 that indicate a localized region of high pressure. In an embodiment, a high-pressure region-of-interest (ROI) is calculated using operation 530, FIG. 5. Another example of the first limit is a pressure profile that indicates poor posture by the user. In an embodiment, a posture score is determined using operation 540, FIG. 5.

In a step 440, a cumulative pressure profile is determined. The cumulative pressure profile is determined from the pressure profile of step 420 monitored over time for a duration. In an example of step 440, the pressure profile is monitored for a predetermined duration and controller 120 determines the cumulative pressure profile based on operation 550, FIG. 5. The cumulative pressure profile may be used to determine when adjustments or additional comfort measures are needed due to long durations, even for acceptable positions. In other words, pressure profiles determined in step 430 that do not exceed the first limit may eventually necessitate position adjustments or additional comfort measures.

Step 450 is a decision. If in step 450 the cumulative pressure profile exceeds a second limit, method 400 proceeds to step 460 to adjust the system configuration. Otherwise, method 400 returns to step 440 to repeat determining a cumulative pressure profile. In other words, the cumulative pressure profile is updated over time until the second limit is exceeded. The frequency with which step 440 is repeated, thereby updating the cumulative pressure profile, may depend on such things as the duration of the flight, a customization for a specific user, or some other factor. For example, step 440 may be repeated with increasing frequency over time. In other words, the predetermined duration may decrease with increasing repetition of steps 440 and 450.

In an example of step 450, regions of moderate pressure that do not exceed the first limit in step 430, may during the predetermined duration have a cumulative effect that exceeds the second limit necessitating a position adjustment or other comfort measure. In another example where the first limit is not exceeded in step 430, the cumulative effect during the predetermined duration may not initially exceed the second limit in step 450, but the cumulative effect may eventually exceed the second limit following one or more repetitions of steps 440 and 450.

In a step 460, system configuration is adjusted. In an example of step 460, configuration of system 100, FIG. 1 is adjusted based on the pressure profile determined in step 420 or the cumulative pressure profile determined in step 440. System configuration adjustments may be determined using operation 560, FIG. 5, for example. In an embodiment, system 100 may adjust its configuration by adjusting one or more of lower back curvature via lumbar support 130, firmness via air bladders 140, tilt or position via motors 150, massage via massagers 160, and temperature via thermal therapy unit 170.

In an optional step 470, method 400 returns to step 410 to repeat automatically adjusting the comfort system. Once a seating or lying configuration is adjusted, the pressure profile is again determined and monitored over time to determine if and when a subsequent adjustment is needed. During long durations, the period for determining when an adjustment is needed may become iteratively shorter due to the cumulative effect of sitting or lying on discomfort.

Figure 5:
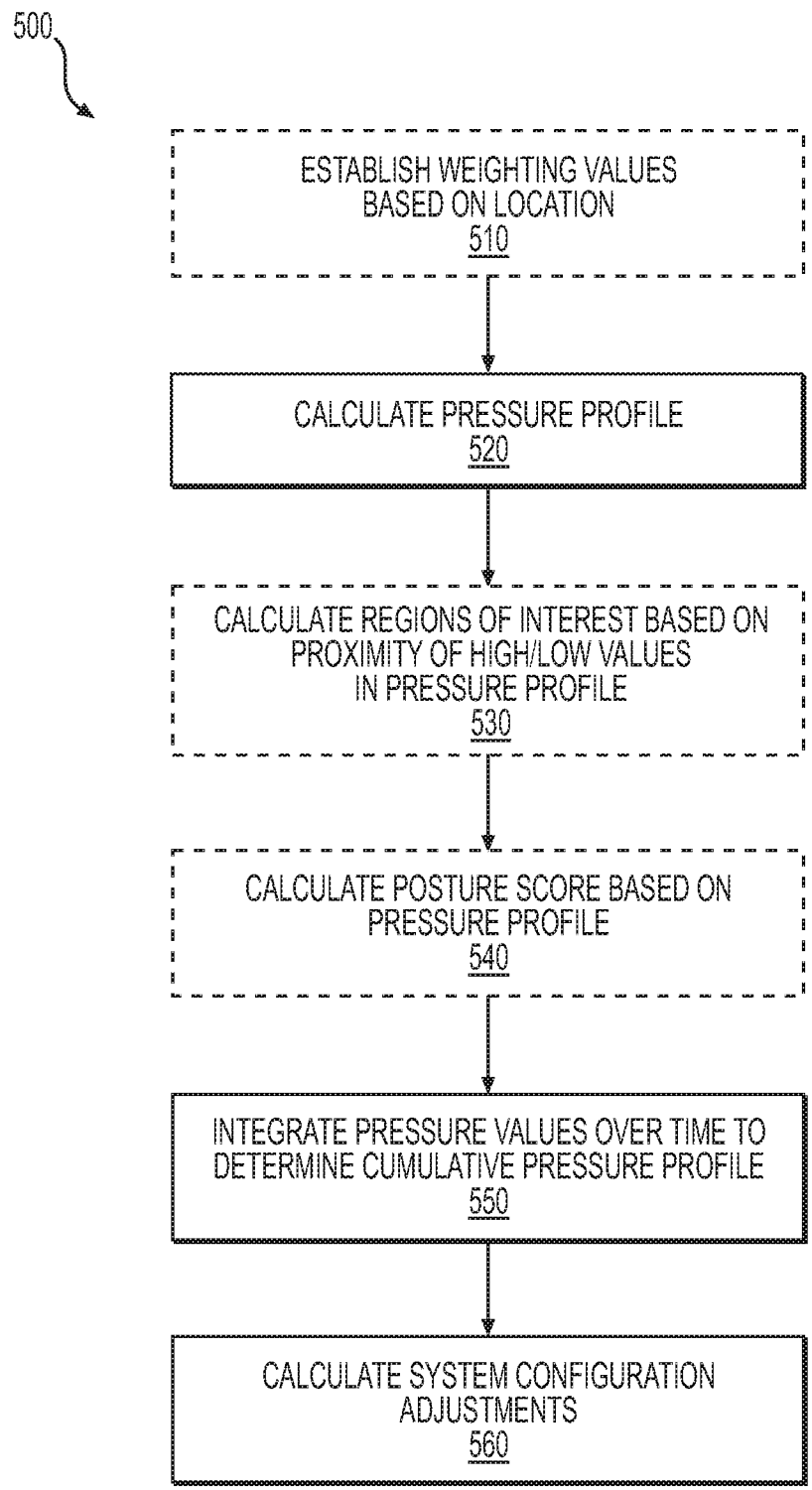
FIG. 5 is a block diagram of a control algorithm used by the automatically adjusting comfort system of FIG. 1.

FIG. 5 is a block diagram of a control algorithm 500 used by the automatically adjusting comfort system 100, FIG. 1. Algorithm 500 is provided by instructions of software 125 to determine a pressure profile that includes data from each of the sensors of pressure-sensor array 110, and a cumulative pressure profile, that monitors the pressure profile over time. One or more operations of algorithm 500 may be used by various steps of method 400 described above. Without departing from the scope hereof, operations of algorithm 500 may be performed individually or in various alternate sequences from the order shown in FIG. 5.

In an optional operation 510, weighting values are established based on location. In an example of operation 510, controller 120 uses software 125 to establish weighting values based on measurement locations within pressure-sensor array 110. For example, weighting values established for pressure sensors located in seat bottom 290 may be higher than those for seat back 280 due to more weight of the user being applied to the seat bottom. Weighting values may include constant or variable values stored in a lookup table, equations, formulas, probability distributions, etc. For example, weighting values for pressure sensors located in seat bottom 290 and seat back 280 may vary depending on a position or configuration of the seat (e.g., for an upright versus a reclined seating position).

In an operation 520, a pressure profile is calculated. In an example of operation 520, processor 122 executes software 125 that includes one or more formulas and/or mathematical expressions, which are stored in memory 124, to calculate a pressure profile based on values from pressure-sensor array 110 and optionally weighting values established in operation 510. Operation 520 may be used to determine a pressure profile, as in step 420, FIG. 4, for example. In certain embodiments, the pressure profile is a pressure distribution having corresponding pressure statistics (e.g., mean, median, standard deviation, etc.). In certain other embodiments, the pressure profile may be expressed as a pressure map having contours or other visual elements used to display pressure values over an area. The pressure map may optionally be displayed to a user via interface 126, for example.

In an optional operation 530, regions-of-interest (ROIs) are calculated based on proximity of differential values in the pressure profile. In other words, groupings of nearby high-pressure or low-pressure values compared to a baseline pressure value may be identified as ROIs. In an example of operation 530, processor 122 executes software 125 that includes one or more formulas and/or mathematical expressions, which are stored in memory 124, to calculate ROIs from the pressure profile or map determined in operation 520. In certain embodiments, the pressure values used to determine ROIs may be based on weighted-pressure values to account for expected pressure distributions and thus avoid false-positive identifications (e.g., pressure applied to a seat bottom may be higher than pressure applied to a seat back under normal seating conditions). ROIs may be used to identify high-pressure and low-pressure zones based on a relative difference or ratio of the ROI compared to neighboring regions. In certain embodiments, the ROIs are identified based on a predetermined percent difference compared to a baseline weighted-pressure value. The baseline weighted-pressure value may be an average or median pressure value of the pressure profile, for example, or some other statistical or predetermined pressure value. In an embodiment, regions of user discomfort may be predicted based on ROIs calculated using operation 530.

In an optional operation 540, a posture score is determined based on the weighted pressure profile. In an example of operation 540, processor 122 executes software 125 that includes one or more formulas and/or mathematical expressions, which are stored in memory 124, to calculate a posture score indicative of a user's posture that is based on the pressure profile determined in operation 520. A low posture score may be used to determine if a pressure profile exceeds a limit (e.g., such as the first limit in step 430, FIG. 4). In an embodiment, a low posture score is indicative of poor posture, which may be used to predict discomfort.

In an operation 550, pressure values are integrated over time to determine a cumulative pressure profile. In an example of operation 550, processor 122 executes software 125 that includes one or more formulas and/or mathematical expressions, which are stored in memory 124, to calculate integrated pressure values based on a duration. In certain embodiments, weighted-pressure values may be integrated over time to determine the cumulative pressure profile to avoid false-positive identifications based on expected pressure distributions. Integrated pressure values may be used to determine if the cumulative pressure profile exceeds a limit (e.g., such as the second limit in step 450, FIG. 4).

In an operation 560, system configuration adjustments are calculated. In an example of operation 560, processor 122 executes software 125 that includes one or more formulas and/or mathematical expressions, which are stored in memory 124, to calculate adjustments to system 100, as in step 460, FIG. 4. Configuration adjustments may include changes to one or more components to avert discomfort (e.g., lumbar support 130, air bladders 140, position motors 150, massagers 160, and thermal therapy 170, FIG. 1), which are automatically controlled via controller 120. In certain embodiments, the configuration adjustments are adapted to reduce the magnitude of regions of differential pressure. For example, the configuration adjustments are adapted to reduce high pressure ROIs or increase low pressure ROIs identified in step 530.

In certain embodiments, method 500 is customized for an individual user. For example, instantaneous and cumulative pressure limits may be adjusted for individual users. Custom algorithms for individual users may be developed to take into consideration such factors as the weight of the user (e.g., a heavier user may have a higher-pressure threshold), a particular sensitivity of the user (e.g., a susceptibility to poor posture), or a personal preference (e.g., a preference to be warm or cool).

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Not all operations listed in the various figures need be carried out in the specific order described.

We claim:

1. An automatically adjusting comfort method, comprising:
    measuring pressure applied by a user to a first surface via a pressure-sensor array comprising a plurality of individual pressure sensors;
    receiving pressure data from the pressure sensor array via a controller;
    determining, via the controller, weighted-pressure values based on measurements from the pressure-sensor array in combination with a location of each of the individual pressure sensors on the first surface;
    comparing, via the controller, the weighted-pressure values to a first limit, wherein the first limit is a predetermined weighted-pressure value;
    determining, via the controller, cumulative pressure values by integrating the weighted-pressure values over an initial duration;
    comparing, via the controller, the cumulative pressure values to a second limit wherein the second limit is a predetermined cumulative pressure value;
    adjusting one or more of a plurality of adjusting mechanisms configured to alter the weighted-pressure values for increased comfort of the user when the pressure profile exceeds the first limit or the second limit;
    repeating the step of determining the cumulative pressure values with increasing frequency such that the duration for integrating the weighted-pressure values is decrease from the initial duration to become iteratively shorter and the second limit is decreased;
    determining one or more regions of interest based on the weighted-pressure values from a group of individual pressure sensors in proximity, wherein each of the one or more regions of interest includes groupings of high-pressure or low-pressure values that collectively deviate from a median weighted-pressure value; and
    adjusting one or more of the plurality of adjusting mechanisms to reduce pressure at high-pressure regions of interest or to increase pressure at low-pressure regions of interest.

2. The method of claim 1, further comprising measuring, via the controller, pressure applied by the user to a second surface via the pressure-sensor array.

3. The method of claim 2, further comprising calculating, via the controller, pressure profiles of the first surface and the second surface; and
    adjusting one or more of a plurality of adjusting mechanisms based on a ratio of the pressure profiles.

4. The method of claim 1, further comprising: predicting one or more regions of user discomfort, via the controller, based on the one or more regions of interest.

5. The method of claim 1, wherein determining a cumulative pressure value comprises integrating weighted-pressure values over time for the predetermined duration, via the controller.

6. The method of claim 1, wherein adjusting one or more of the plurality of adjusting mechanisms includes adjusting one or more of position motors, massagers, lumbar supports, and inflating or deflating air bladders.

7. The method of claim 6, further comprising providing a custom configuration by setting the first limit and the second limit according to a custom algorithm determined for a particular user.

8. An automatically adjusting comfort system, comprising:
- a pressure-sensor array in or beneath an outer fabric of a seat;
- a controller communicatively coupled to the pressure sensor array, the controller being configured for determining:
  - a) a cumulative pressure profile by integrating pressure values from the pressure sensor array over time; and
  - b) a region of high or low pressure based on pressure values from a grouping of nearby pressure sensors in the pressure-sensor array; and
  - c) a pressure map comprising contour lines to display a pressure distribution, wherein the contour lines indicate pressure values interpolated between individual sensors of the pressure-sensor array for indicating the region of high or low pressure;
- a plurality of adjusting mechanisms configured to alter the cumulative pressure profile and the region of high or low pressure to increase a user's comfort, wherein the controller automatically adjusts one or more of the plurality of adjusting mechanisms; and
- a user interface configured to display the pressure map.

9. The system of claim 8, wherein the plurality of adjusting mechanisms comprise air bladders, position motors, and lumbar supports.

10. The system of claim 8, wherein the plurality of adjusting mechanisms are configured to adjust firmness, lumbar support, posture, and temperature based on the cumulative pressure profile.

11. The system of claim 8, wherein the pressure-sensor array is integrated into a seat such that individual pressure sensors are positioned along a top surface of a seat bottom and a forward-facing surface of a seat back for measuring pressure applied by a user seated in the seat.

12. The system of claim 11, wherein the seat is a pilot seat or a co-pilot seat onboard an aircraft and the controller is configured to maintain comfort of the pilot seat or the co-pilot seat during long-duration flights by automatically adjusting one or more of the plurality of adjusting mechanisms based on the cumulative pressure profile or the region of high or low pressure.

13. A method of automatically maintaining comfort for extended duration while seated, comprising:
- measuring pressure applied to a surface of a seat via an array of pressure sensors to determine an array of pressure values in real-time via a controller;
- weighting the pressure values, via the controller, based on measurements from the array of pressure sensors in combination with locations on the surface of corresponding pressure sensors of the array to determine weighted-pressure values;
- determining one or more regions of differential pressure, via the controller, based on the weighted-pressure values for groupings of pressure sensors in proximity with one another for an initial duration;
- adjusting a configuration of the seat for reducing a magnitude of the differential pressure at the one or more regions;
- after the initial duration, determining a cumulative pressure profile, via the controller, by integrating the weighted-pressure values over a second duration;
- repeating the step of determining the cumulative pressure profile for an iteratively shorter duration than the second duration due to a cumulative effect on discomfort of the user; and
- adjusting a configuration of the seat for maintaining comfort based on the cumulative pressure profile.

14. The method of claim 13, further comprising determining a pressure distribution, via the controller, based on the array of pressure values.

15. The method of claim 13, further comprising determining a pressure map based on the array of pressure values and displaying contours of the pressure map on a user interface.

16. The method of claim 13, further comprising adjusting a configuration of the seat for maintaining comfort based on one or more of the cumulative pressure profile, a pressure map, a pressure distribution, and personal preferences of a user.

17. The method of claim 16, wherein adjusting the configuration of the seat comprises adjusting components of the seat to adjust one or more of firmness, lumbar support, body position, posture, and temperature.

18. The system of claim 8, further comprising massagers located internally to increase a user's comfort by massaging a user's muscles.

19. The system of claim 8, further comprising a thermal therapy unit, wherein the thermal therapy unit comprises:
- at least one bladder located in the seat;
- a pump to circulate a fluid between a reservoir and the at least one bladder;
- a heater and a chiller coupled to the reservoir for controlling a temperature of the fluid; and
- valves for directing fluid from the reservoir to the at least one bladder based on the region of high or low pressure to increase a user's comfort.

20. The method of claim 1, wherein determining the one or more regions of interest comprises identifying groupings of weighted-pressure values that collectively deviate from the median weighted-pressure value by two standard-deviations.

* * * * *